United States Patent
Su et al.

(10) Patent No.: US 10,928,300 B2
(45) Date of Patent: Feb. 23, 2021

(54) EXPERIMENTAL DEVICE AND EXPERIMENTAL METHOD FOR TESTING THE LUBRICITY IN HORIZONTAL WELL DRILLING WITH A CUTTINGS BED TAKEN INTO CONSIDERATION

(71) Applicant: Southwest Petroleum University, Chengdu (CN)

(72) Inventors: Junlin Su, Chengdu (CN); Jinjun Huang, Chengdu (CN); Pingya Luo, Chengdu (CN); Fang Li, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 0 days.

(21) Appl. No.: 16/825,984

(22) Filed: Mar. 20, 2020

(65) Prior Publication Data
US 2020/0217780 A1 Jul. 9, 2020

Related U.S. Application Data

(63) Continuation of application No. PCT/CN2018/123185, filed on Dec. 24, 2018.

(30) Foreign Application Priority Data

Aug. 23, 2018 (CN) .......................... 201810964421.4

(51) Int. Cl.
*G01N 33/30* (2006.01)
*E21B 21/08* (2006.01)
(Continued)

(52) U.S. Cl.
CPC ......... *G01N 19/02* (2013.01); *G01N 33/2823* (2013.01); *G01N 33/30* (2013.01)

(58) Field of Classification Search
CPC ............... G01N 19/02; G01N 33/2888; G01N 33/2823; G01N 33/30; G01N 11/00; G01N 33/28; F16N 29/00
See application file for complete search history.

(56) References Cited

U.S. PATENT DOCUMENTS

| 5,586,027 A | * 12/1996 | Carlson .................... G01F 1/74 702/12 |
| 5,969,227 A | 10/1999 | Kenney |
| 2018/0356556 A1 | * 12/2018 | Appel ................ G01N 33/2823 |

FOREIGN PATENT DOCUMENTS

| CN | 204214761 U | 3/2015 |
| CN | 204373896 U | * 6/2015 |

(Continued)

OTHER PUBLICATIONS

English machine translation for CN-204373896-U.*
Search Report and Written Opinion for International Application No. PCT/CN2018/123185 dated Apr. 28, 2019.

*Primary Examiner* — Daniel S Larkin
*Assistant Examiner* — Anthony W Megna Fuentes
(74) *Attorney, Agent, or Firm* — Calfee Halter & Griswold LLP

(57) ABSTRACT

The present invention relates to an experimental device for testing the lubricity in horizontal well drilling with a cuttings bed taken into consideration, which comprises a simulated wellbore with a pulley provided at one end and a hydraulic cylinder fixed and a drill rod mounted at the other end; a cuttings feeding port is arranged above the simulated wellbore; a low end of the simulated wellbore is connected with a liquid return pipeline; the simulated wellbore is provided with an ultrasonic probe and is connected with a rock core holder. The present invention is in line with the actual operating conditions because it not only takes consideration of the friction force between the drill string and the drilling (Continued)

fluid, wellbore wall and slurry cake, but also takes consideration of the friction force between the drill string and the cuttings bed.

9 Claims, 1 Drawing Sheet

(51) Int. Cl.
    *E21B 47/00*     (2012.01)
    *G01N 19/02*     (2006.01)
    *G01N 33/28*     (2006.01)

(56)     References Cited

FOREIGN PATENT DOCUMENTS

| | | |
|---|---|---|
| CN | 105572031 A | 5/2016 |
| CN | 105628600 A | 6/2016 |

* cited by examiner

EXPERIMENTAL DEVICE AND EXPERIMENTAL METHOD FOR TESTING THE LUBRICITY IN HORIZONTAL WELL DRILLING WITH A CUTTINGS BED TAKEN INTO CONSIDERATION

PRIORITY CLAIM & CROSS REFERENCE

This application is a by-pass continuation of and claims priority to PCT/CN2018/123185 filed Dec. 24, 2018, which claims priority to Chinese Application No. 201810964421.4, filed on Aug. 23, 2018, entitled "Horizontal Well Drilling Apparatus For Testing Lubricity And Testing Method, Taking Cuttings Bed Into Account", which are specifically and entirely incorporated by reference.

FIELD

The present disclosure belongs to the field of petroleum drilling, and in particular relates to an experimental device and an experimental method for testing the lubricity in horizontal well drilling with a cuttings bed taken into consideration.

BACKGROUND

In recent years, as oil exploration and development techniques and drilling techniques are developed rapidly, the drilling depth is increased more and more. On the other hand, in order to improve economic and technological benefits, more and more oil and gas wells are drilled as highly deviated and extended-reach directional wells and horizontal wells, which can cover multiple oil and gas reservoirs and realize multiple production in one well. For horizontal wells, one of the major technical difficulties is that it is difficult to carry away the cuttings and the cuttings may accumulate easily to form a cuttings bed and severely decreases the drilling efficiency. In addition, the cuttings bed formed in a horizontal drilling process seriously affects the lubricity in the drilling process because the drill string almost lies on the lower wall of the build-up section and horizontal section.

However, at present, the evaluation and research on the lubricity of drilling fluids in China and foreign countries only consider the friction between the drill string and the drilling fluid, borehole wall rock and slurry cake, but don't take consideration of the friction resistance between the drill string and the cuttings bed. During the drilling, the cuttings bed increases the torque and friction resistance in the drilling and tripping process, resulting in decreased lubricity of the drilling fluid. Consequently, the lubricity of the drilling fluid varies greatly in an indoor environment and in the field, and a drilling fluid formulation designed indoor can't meet the requirements of field drilling.

SUMMARY

The object of the present disclosure is to provide an experimental device and an experimental method for the lubricity in horizontal well drilling considering a cuttings bed. When the device is used for evaluating the lubricity in horizontal well drilling, both the friction force between the drill string and the drilling fluid, borehole wall rock and slurry cake and the friction force between the drill string and the cuttings bed are taken into consideration, and the lubricating coefficient of the drilling fluid between the drill rod and the rock, slurry cake and cuttings bed can be measured.

The technical scheme employed in the present disclosure is as follows:

An experimental device for testing the lubricity in horizontal well drilling with a cuttings bed taken into consideration, comprising a pulley track, a transparent visual simulated wellbore arranged on the pulley track, with a pulley arranged below one end of the simulated wellbore, a hydraulic cylinder fixedly connected below the other end of the simulated wellbore, and a drill rod mounted at the end connected with the hydraulic cylinder, wherein one end of the drill rod extends into the simulated wellbore, the other end of the drill rod is connected with a stepping drive mechanism and a rotating drive mechanism, and the drill rod is also provided with a thrust sensor and a torque sensor;

a cuttings feeding port is arranged above the simulated wellbore and connected to a slurry tank through a liquid feeding pipeline, and a high-pressure pump, a flowmeter B and a pressure sensor are sequentially arranged on the liquid feeding pipeline;

the lower end of the simulated wellbore is connected with a liquid return pipeline leading to the slurry tank, and a temperature-reducing and pressure-reducing mechanism, a flowmeter A and a transfer pump are sequentially arranged on the liquid return pipeline;

an ultrasonic probe for detecting the thickness and flatness of the cuttings bed is arranged on the outer wall of the simulated wellbore, a rock core holder is fixedly connected at the end of the simulated wellbore near the pulley, a heating mechanism is arranged on the upper part of the rock core holder, a rock core is arranged on the lower part of the rock core holder, and a pressure mechanism is arranged at the lower side of the rock core; a cuttings lifting platform is provided at the inner side of the lower wall of the simulated wellbore and connected to a cuttings bed control center.

Furthermore, the power of the hydraulic cylinder comes from a hydraulic pump, which consists of a pump body, a plunger and an operating handle, an oil tank is connected with the hydraulic cylinder and the hydraulic pump through an oil pipe respectively, a check valve is arranged between the oil tank and the hydraulic pump and between the hydraulic pump and the hydraulic cylinder respectively, and a stop valve is arranged between the oil tank and the hydraulic cylinder.

Furthermore, a rubber ring is arranged at the joint between the simulated wellbore and the drill rod for a sealing purpose.

Furthermore, the temperature-reducing and pressure-reducing mechanism is arranged on an initial section of the liquid return pipeline and consists of an electric temperature-reducing and pressure-reducing valve, a safety valve, a pressure meter, a thermometer, a check valve, an electric regulating valve, a throttle valve, a stop valve, a transition pipe, a temperature-reducing water pipe and flange fasteners.

Furthermore, the heating mechanism comprises an electric heating jacket and a temperature controller connected with the electric heating jacket and a temperature sensor respectively, and the heating temperature of the electric heating jacket can be adjusted by means of the temperature controller, thereby the temperature in the visual experimental drilling system can be controlled, and the high-temperature and high-pressure environment of deep well drilling can be simulated.

Furthermore, the inclination angle of the simulated wellbore can be adjusted steplessly within range of 0°-90°.

Furthermore, the pressure mechanism comprises a piston cylinder and a mechanical booster pump for supplying pressure to the piston cylinder, wherein the mechanical booster pump is connected with a rodless cavity end of the piston cylinder, and a piston rod of the piston cylinder passes through the rock core holder and abut against the rock core to provide pressure for friction drilling between the drill rod and a filter cake formed on the surface of the rock core.

Furthermore, a cuttings recovery tank with a filter screen is arranged above the slurry tank, and a stirrer is arranged in the slurry tank.

Furthermore, a differential pressure transmitter for detecting the pressure difference between the two ends of the simulated wellbore is further arranged on the simulated wellbore, wherein connectors at two ends of the differential pressure transmitter are connected to the inner wall of the wellbore through the simulated wellbore to measure the pressure difference between the two ends of the wellbore; the differential pressure transmitter and other detection components such as the pressure sensor, the ultrasonic probe, a flowmeter A, a flowmeter B, the thrust sensor, the torque sensor, a temperature sensor and a temperature controller, etc. are connected to a calculation and display unit through data wires for displaying various detection data and calculating a sliding friction coefficient between the drill rod and the filter cake.

The present disclosure attains the following beneficial effects:

Compared with the methods in the prior art in China and foreign countries, the present disclosure has the following advantages when it is used in experiments for evaluating the lubricity of drilling fluid in horizontal well drilling:

By employing a visual experimental drilling system, the state of the cuttings bed and the drilling condition of the drill rod can be observed in real time in the compound drilling process for simulating slide drilling and rotary drilling with the drill rod, thus a shortcoming that the underground condition can only be reckoned through theoretical calculation and analysis in the prior art is overcome;

The drilling fluid supply system can simulate drilling environments at different temperatures and pressures, especially high-temperature and high-pressure environments, by adjusting the pressure and formulation of the drilling fluid and employing a heating mechanism for assistance; the drilling fluid and cuttings can be recycled through a circulation pipeline;

By arranging a hydraulic lifting device at one end of the simulated wellbore, the inclination angle of the wellbore can be adjusted steplessly within a range of 0°-90°; by arranging a cuttings bed, a sliding friction coefficient between the drill rod and the slurry cake and cuttings bed can be measured comprehensively, thus a shortcoming that only the friction force between the drill rod and the slurry cake can be simulated in the prior art is overcome, the simulation result is more in line with the actual underground condition, and the simulation result can be displayed in real time on a calculation and display unit.

With the flowmeter, thrust sensor, torque sensor, temperature sensor, pressure sensor, temperature controller, differential pressure transmitter, ultrasonic probe and other detection components, the simulation result can be analyzed more accurately and quantitatively.

In addition, the experimental device may be made into a full-size wellbore, and the formulation of the drilling fluid and the cuttings parameters can be adjusted to carry out simulation of a full-size wellbore under different working conditions.

An evaluation method for torque, thrust-cuttings bed-lubricity is established with the device. The torque parameter and thrust parameter that can be obtained the most easily in field construction are used as the main indexes for evaluating the lubricity of the drilling fluid. A sliding friction coefficient between the drill rod and the cuttings bed and slurry cake can be reflected according to the change of the rotational torque and thrust of the drill rod, thus the evaluation efficiency can be improved greatly.

In the figures: 1—stepping drive mechanism; 2—thrust sensor; 3—torque sensor; 4—rotating drive mechanism; 5—drill rod; 6—ultrasonic probe; 7—cuttings lifting platform; 8—simulated wellbore; 9—cuttings feeding port; 10—electric heating jacket; 11—rock core; 12—piston cylinder; 13—rock core holder; 14—temperature sensor; 15—temperature controller; 16—pulley; 17—pulley track; 18—liquid feeding pipeline; 19—pressure sensor; 20—cuttings bed control center; 21—mechanical booster pump; 22—flowmeter B; 23—high-pressure pump; 24—slurry tank; 25—stirrer; 26—liquid return pipeline; 27—cuttings recovery tank; 28—transfer pump; 29—temperature-reducing and pressure-reducing mechanism; 30—differential pressure transmitter; 31—calculation and display unit; 32—stop valve; 33—oil tank; 34—first check valve; 35—plunger; 36—pump body; 37—operating handle; 38—hydraulic cylinder; 39—second check valve; 40—rubber ring.

DETAILED DESCRIPTION

Hereafter the present disclosure will be further detailed in specific examples, with reference to the accompanying drawings.

Figure 1:
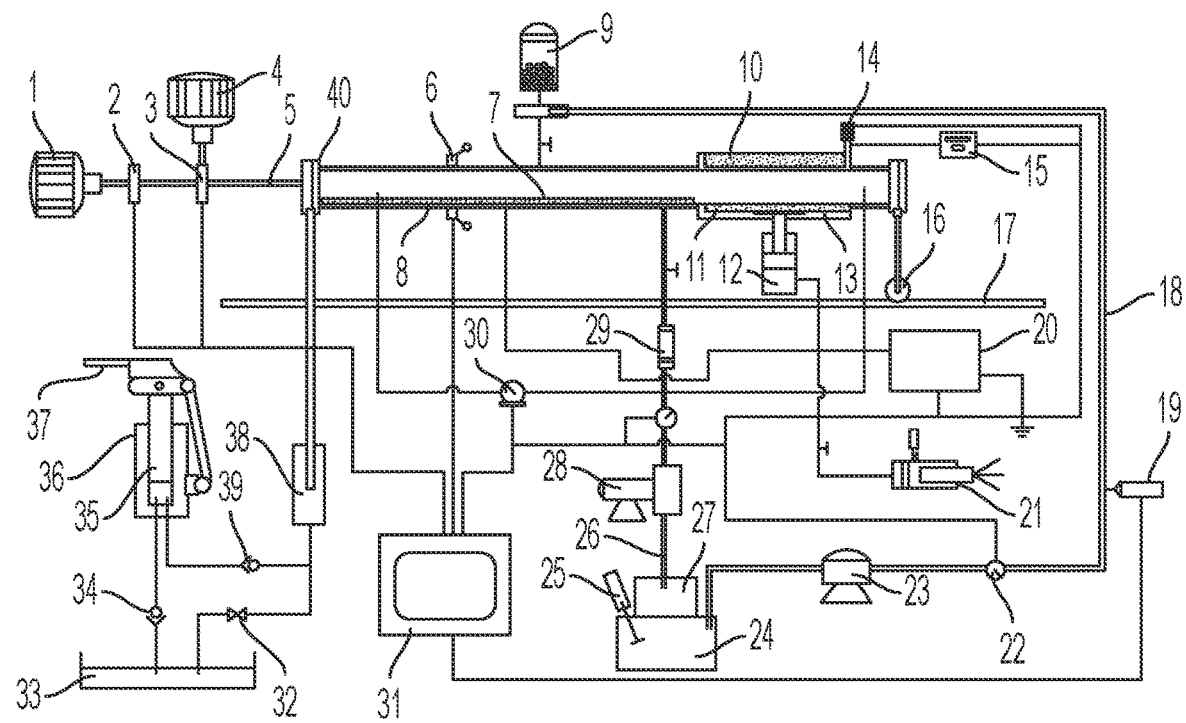
FIG. 1 is a schematic diagram of the connection structural of the device in the present disclosure.
Figure 2:
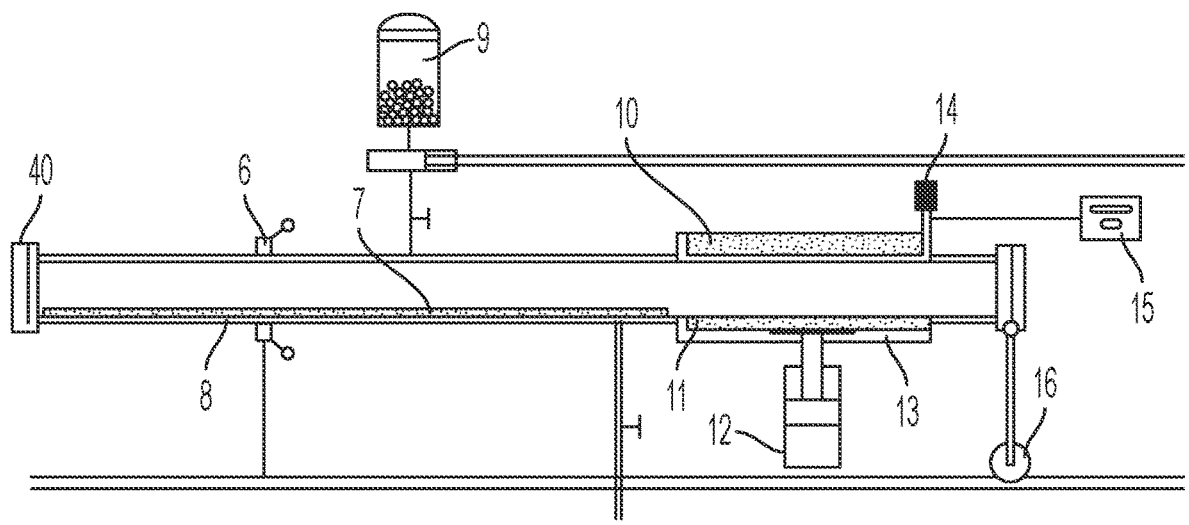
FIG. 2 is an enlarged view of a simulated wellbore and a rock core holder.

As set forth in FIG. 1, an experimental device for testing the lubricity in horizontal well drilling with a cuttings bed taken into consideration comprises a visual experimental drilling system, a hydraulic lifting device, a drilling fluid supply system, a pressure mechanism and a calculation and display unit, wherein the visual drilling experimental system can withstand temperature above 200° C. and pressure above 30 MPa, and a compound drilling method integrating rotary drilling and slide drilling can well simulate a cuttings bed state under actual operating conditions. Therefore, the experimental compound drilling system can simulate the lubricity of drilling fluid in deep well drilling at certain temperature and pressure under conditions that are closer to field operating conditions.

The specific connection structure of the experimental device and the functions of the components are described as follows:

An experimental device for testing the lubricity in horizontal well drilling with a cuttings bed taken into consideration, comprising a pulley track 17, a transparent visual simulated wellbore 8 arranged on the pulley track 17, with a pulley 16 arranged below one end of the simulated wellbore 8, a hydraulic cylinder 38 fixedly connected below the other end of the simulated wellbore for changing the inclination angle of the wellbore, and a drill rod 5 mounted at the end connected with the hydraulic cylinder, wherein one end of the drill rod extends into the simulated wellbore 8, the other end of the drill rod is connected with a stepping drive mechanism 1 and a rotating drive mechanism 4 for simulating a rotary drilling process, and the drill rod 5 is also provided with a thrust sensor 2 and a torque sensor 3;

A sealing rubber ring 40 is arranged at the joint between the drill rod 5 and the simulated wellbore 8 to prevent drilling fluid leakage and wellbore pressure leakage when the drill rod drills in the visual experimental drilling system. One end of the simulated wellbore is hinged with a plunger of the hydraulic cylinder, and the other end of the simulated wellbore is hinged with the pulley support. The pulley is fixed on the pulley track via a groove. When the hydraulic lifting device lifts one end of the simulated wellbore, it will pull the other end of the simulated wellbore to slide on the pulley track, thus the inclination angle of the wellbore can be adjusted steplessly within a range of 0°-90°.

The power of the hydraulic cylinder 38 comes from a hydraulic pump, which consists of a pump body 36, a plunger 35 and an operating handle 37, an oil tank 33 is connected with the hydraulic cylinder and the hydraulic pump through an oil pipe respectively, a check valve 34 is arranged between the oil tank 33 and the hydraulic pump and between the hydraulic pump and the hydraulic cylinder respectively, and a stop valve 32 is arranged between the oil tank and the hydraulic cylinder. The oil injected into the hydraulic cylinder from the hydraulic pump and the oil injected into the hydraulic pump from the oil tank can't flow back. To relieve the pressure in the hydraulic cylinder, the stop valve between the oil tank and the hydraulic cylinder may be opened; then the returned oil is stored in the oil tank. The plunger of the hydraulic cylinder is hingedly connected to one end of the simulated wellbore, so that the angle can be changed freely at the joint between the plunger and the simulated wellbore. The hydraulic cylinder is in a fixed state, and the driving mechanism of the drill rod is constrained by the simulated wellbore and moves along with the simulated wellbore.

A cuttings feeding port 9 is arranged in the upper part of the simulated wellbore 8 and connected to a slurry tank 24 through a liquid feeding pipeline 18. A high-pressure pump 23, a flowmeter B 22 and a pressure sensor 19 are arranged on the liquid feeding pipeline to provide high-pressure slurry in the entire simulated drilling process, and the pressure in the simulated wellbore can be changed by controlling the power of the high-pressure pump.

The lower end of the simulated wellbore is connected with a liquid return pipeline 26 leading to the slurry tank, and a temperature-reducing and pressure-reducing mechanism 29, a flowmeter A and a transfer pump 28 are arranged on the liquid return pipeline. The drilling fluid enters the simulated wellbore 8 of the visual experimental drilling system through the liquid feeding pipeline 18, and then flows into the slurry tank 24 through the liquid return pipeline 26. In the process that the drilling fluid flows out of the simulated wellbore into the slurry tank, the slurry with cuttings is treated by the temperature-reducing and pressure-reducing mechanism 29, so as to simulate the temperature change of the slurry in actual well drilling more truly, in view that the temperature of the slurry is greatly reduced when the slurry flows back into the slurry tank in actual well drilling but the return path of the device is too short to reduce the temperature naturally and rapidly. By utilizing a special temperature-reducing mechanism, the temperature is more in line with that in the actual situation; through return flow, the drilling fluid can be dynamically circulated; cuttings different in lithology, size and structure may be loaded into the simulated wellbore through the cuttings feeding port; in addition, a cuttings recovery tank 27 with a filter screen is arranged above the slurry tank 24, and a stirrer 25 is arranged in the slurry tank. The stirrer stirs the drilling fluid in the slurry tank in real time to ensure that the drilling fluid flowing out in different time periods is fully mixed and is relatively uniform; the temperature-reducing and pressure-reducing mechanism 29 is arranged on an initial section of the liquid return pipeline and consists of an electric temperature-reducing and pressure-reducing valve, a safety valve, a pressure meter, a thermometer, a check valve, an electric regulating valve, a throttle valve, a stop valve, a transition pipe, a temperature-reducing water pipe and flange fasteners. After the through-flow area is changed by means of the throttle valve, the pressure difference is altered. The temperature reduction is mainly realized by heat exchange with the cold water in the temperature-reducing water pipe.

An ultrasonic probe 6 for detecting the thickness and flatness of the cuttings bed is arranged on the outer wall of the simulated wellbore, a rock core holder 13 is fixedly connected to the end of the simulated wellbore near the pulley 16, a heating mechanism is arranged on the upper part of the rock core holder, a rock core 11 is arranged on the lower part of the rock core holder, and a pressure mechanism is arranged at the lower side of the rock core. In a simulated drilling process, the pressure mechanism applies pressure upwards to increase the friction force between the drill rod and a filter cake formed on the surface of the rock core, and thereby the pressure loss contribution of the filter cake in the drilling process is simulated; a cuttings lifting platform 7 is arranged at the inner side of the lower wall of the simulated wellbore and connected to a cuttings bed control center 20, for receiving deposited cuttings and adjusting the thickness of the cuttings bed, so as to simulate a drilling tool jamming phenomenon resulted from local cuttings accumulation during actual construction as well as simulate the drilling friction force resulted from the cuttings bed at different levels of accumulation and flatness.

The heating mechanism comprises an electric heating jacket 10 and a temperature controller 15 for adjusting the heating temperature of the electric heating jacket so as to control the temperature in the visual experimental drilling system and simulate a high-temperature and high-pressure environment of deep well drilling; the pressure mechanism comprises a piston cylinder 12 and a mechanical booster pump 21 for supplying pressure to the piston cylinder, wherein the mechanical booster pump 21 is connected with a rodless cavity end of the piston cylinder 12, and a piston rod of the piston cylinder passes through the rock core holder 13 and abuts against the rock core 11 to provide pressure for friction drilling between the drill rod and a filter cake formed on the surface of the core; the pressure of the piston cylinder on the rock core can be adjusted by adjusting the mechanical booster pump, and thereby the magnitude of the abutting force and pressure between the drill rod and the filter cake formed on the surface of the rock core can be adjusted.

A differential pressure transmitter 30 for detecting the pressure difference between the two ends of the simulated wellbore is further arranged on the simulated wellbore, wherein connectors at two ends of the differential pressure transmitter are connected to the inner wall of the wellbore through the simulated wellbore to measure the pressure difference between the two ends of the wellbore; the differential pressure transmitter 30 and other detection components such as the pressure sensor 19, the ultrasonic probe 6, the flowmeter A, the flowmeter B 22, the thrust sensor 2, the torque sensor 3, the temperature sensor 14 and the temperature controller 15, etc. are connected to a calculation and display unit 31 through data wires for displaying various detection data and calculating a sliding friction coefficient between the drill rod and the filter cake.

The process and principle of the device in the present disclosure for evaluating lubricity are as follows: After the cuttings are loaded through the sealed cuttings feeding port, the feeding port is tightly closed with a cover with a sealing rubber ring, the cuttings are carried into the simulated wellbore by the high-pressure drilling fluid flowing below them, and are accumulated on the cuttings lifting platform below the simulated wellbore under the action of gravity and form a cuttings bed. After the drilling fluid is pressurized by the high-pressure pump, the drilling fluid flows through the flowmeter and the pressure sensor and enters the simulated wellbore. In that process, the flow rate and pressure of the drilling fluid can be observed with the flowmeter and the pressure sensor, and the drilling fluid in the visual experimental drilling system can be properly adjusted by adjusting the parameters of the high-pressure pump and the heating mechanism, so that the temperature and pressure reach predetermined values; after the thickness and flatness of the cuttings accumulated in the simulated wellbore reach predetermined values and the drilling fluid forms a slurry cake in certain thickness on the surface of the rock core (the formation process of the slurry cake is as follows: the stepping drive mechanism and the rotating drive mechanism drive the drill rod to perform rotary drilling and slide drilling in the rock core held by the rock core holder; in the friction drilling process, an annular space for supplying the drilling fluid exists between the rock core and the drill rod, and a filter cake will be formed on the surface of the core when the drilling fluid enters the space; pressure for friction drilling between the drill rod and the filter cake formed on the surface of the rock core is provided by the pressure mechanism, and the acting force of the piston cylinder on the rock core can be adjusted by adjusting the mechanical booster pump, so as to adjust the abutting force or pressure between the drill rod and the filter cake formed on the surface of the rock core, wherein the filter cake formed on the surface of a permeable rock core is a necessary condition for sliding friction between the drill rod and the surface of the rock core, and the formation of the filter cake is an inevitable result), the inclination angle of the wellbore is adjusted by means of the hydraulic lifting device, and then the power of the stepping drive mechanism and the rotating drive mechanism is changed to change the drilling speed, and compound drilling can be carried out under conditions close to the actual operating conditions; then the valve of the liquid return pipeline below the simulated wellbore is opened, so that the drilling fluid carries the cuttings and flows through the temperature reducing and pressure reducing mechanism and the flowmeters, and the drilling fluid with the cuttings is transferred by the transfer pump to the cuttings recovery tank and the slurry recovery tank, the cuttings are blocked by the filter screen in the upper cuttings recovery tank, while the drilling fluid flows into the lower slurry recovery tank; loading the cuttings and the drilling fluid into the simulated wellbore again after the treatment to ensure that there is dynamically circulated drilling fluid in the visual experimental drilling system.

The calculation and display unit mainly comprises detection units and a calculation unit, wherein the detection units comprise a torque sensor, a thrust sensor, a pressure sensor, a temperature sensor, a flowmeter, an ultrasonic probe and a differential pressure transmitter, and all of the detection units are connected to a display unit. After the torque and thrust are detected and obtained by means of the torque sensor and thrust sensor, the signals are processed and amplified by means of the signal gain elements in the device and then displayed on the data display unit in real time. Besides, the calculation and display unit is further provided with an alarm device, which automatically gives off an alarm in a case of drilling tool jamming or torque overload incurred by the cuttings when the drilling tool is lifted or lowered. In addition, the detected parameters such as the torque and thrust of the drill rod, thickness and flatness of the cuttings bed, pressure and flow rate of the drilling fluid, and temperature of the visual drilling system, etc. are automatically inputted to professional software to obtain a sliding friction coefficient between the drill rod and the drilling fluid, cuttings bed and rock core.

The specific experimental method in this example is as follows:

A prepared drilling fluid system is loaded into the slurry tank 24, then the high-pressure pump 23 is started to inject the drilling fluid into the liquid feeding pipeline 18, and the power and displacement of the high-pressure pump 23 are adjusted, so that the indicated value of the flowmeter B 22 is 10 L/min. and the indicated value of the pressure sensor 19 is 2.1 MPa.

After the drilling fluid enters the simulated wellbore 8, the valve below the cuttings feeding port 9 is opened, white quartz sand in particle size of 3.4-5.1 mm is loaded into the cuttings feeding port as simulated cuttings in advance, and the cuttings feeding port is sealed by means of the sealing rubber ring 40; after the valve is opened, the simulated cuttings enter the simulated wellbore along with the drilling fluid, deposit under the action of gravity, and form a cuttings bed on the cuttings lifting platform 7; a simulated wellbore cover is arranged at the left end of the cuttings lifting platform 7, a rock core 11 is held at the right end of the cuttings lifting platform 7, and they form a groove together with the cuttings lifting platform 7; the thickness of the cuttings bed can be controlled by adjusting the height of the cuttings lifting platform 7. Specifically, the thickness of the accumulated cuttings bed becomes smaller when the cuttings lifting platform 7 is lifted; otherwise the thickness of the cuttings bed becomes greater; moreover, the thickness of the cuttings bed may be monitored in real time by means of the ultrasonic probe 6 to facilitate adjustment and correction.

The thickness of the cuttings bed is adjusted to about 5 cm, the simulated wellbore 8 is heated by means of the electric heating jacket 10 and adjusting the temperature controller 15; when the temperature in the wellbore measured by the temperature sensor 14 is 60° C., the stepping drive mechanism 1 and the rotating drive mechanism 4 are started, wherein the mechanical rotation speed of the rotating drive mechanism 4 is 50 r/min., and the holding torque of the stepping drive mechanism 1 is 20 N·m; the mechanical booster pump 21 is started to provide pressure to the piston cylinder 12, so that the rock core holder 13 holds the rock core 11 firmly, and provides abutment force and positive pressure to the drill rod 5 and the rock core 11, so that the drill rod 5 forms a slurry cake on the surface of the rock core 11 and has sliding friction with the slurry cake.

The drill bit starts to drill into the rock core. In that process, the drill rod 5 always has been sliding friction with the cuttings bed. Under the action of resistance, the drilling speed of the rotating drive mechanism 4 is smaller than the initial drilling speed 50 r/min. The friction resistance parameter is detected by the thrust sensor 2 and the torque sensor 3 and transmitted to the calculation and display unit 31, and then is calculated and outputted by professional software.

The circulated drilling fluid carries a part of the simulated cuttings into the liquid return pipeline 26, and the temperature and pressure of the drilling fluid are reduced by the temperature-reducing and pressure-reducing mechanism 29, so that the temperature of the circulated drilling fluid is lowered to room temperature and the pressure is lowered to about normal pressure to avoid splashing. The indicated value of the flowmeter in the liquid return line is also 10 L/min., indicating that the entire circulation system is not blocked. The circulated drilling fluid is transferred to the cuttings recovery tank 27 by the transfer pump 28. A slurry tank 24 is arranged below the cuttings recovery tank 27 and a filter screen is provided between the slurry tank 24 and the is monitored with the thrust sensor 2 and torque sensor 3 in real time, and lubrication coefficients are obtained by calculation with the professional software program, as shown in Table 1 (the basic principle is: when an object slides on the surface of another object, the friction force generated is proportional to the vertical force acting on the friction surface, expressed by a formula $f=\mu P$, where f is the friction force, P is the vertical force acting on the surface of the object, is a friction coefficient, and is referred to as a friction resistance coefficient in drilling fluid). In Table 1, the formulation A is 5% bentonite+0.24% $NaCO_3$+0.2% FA367+0.3% JT888+0.1% XY-27.

TABLE 1

Experimental Data and Results

| Formulation of drilling fluid | Whether A cuttings bed is formed? | Type and particle size of cuttings | Thickness of cuttings bed | inclination angle of well bore | Mechanical Holding torque of stepping drive mechanism | Mechanical rotation speed of rotating drive mechanism | Temperature in simulated wellbore | Pressure in simulated wellbore | Flow rate of drilling fluid | Lubricity of drilling fluid Lubrication coefficient of rotation $K_R$ | Lubricity of drilling fluid Lubrication coefficient of lifting $K_L$ |
|---|---|---|---|---|---|---|---|---|---|---|---|
| Formulation A + 1% RT443A | Y | φ3.4~5.1 mm white quartz sand | 5 cm | 45° | 20N·m | 50 r/min | 60° C. | 2.1 MPa | 10 L/min | 0.427 | 0.613 |
| Formulation A + 1% RT443A | N | — | — | 45° | 20N·m | 50 r/min | 60° C. | 2.1 MPa | 10 L/min | 0.043 | 0.126 |
| Formulation A | Y | φ3.4~5.1 mm white quartz sand | 5 cm | 45° | 20N·m | 50 r/min | 60° C. | 2.1 MPa | 10 L/min | 0.735 | 0.948 |
| Formulation A | N | — | — | 45° | 20N·m | 50 r/min | 60° C. | 2.1 MPa | 10 L/min | 0.242 | 0.372 | cuttings recovery tank 27. The simulated cuttings carried by the drilling fluid are blocked by the filter screen in the cuttings recovery tank 27, while the drilling fluid flows into the slurry tank 24 below.

After the stop valve 32 is closed, the operating handle 37 is pulled up and pressed down to pump the hydraulic oil in the oil tank 33 into the hydraulic cylinder 38. Since the check valve 34 prevents backflow, the hydraulic oil in the hydraulic cylinder 38 lifts the plunger upwards. As a result, the left end of the simulated wellbore is raised upwards, the simulated wellbore is tilted and the inclination angle of the wellbore becomes smaller. A pulley 16 is mounted at the right end of the simulated wellbore. Since the left end of the simulated wellbore is horizontally fixed, the right end of the simulated wellbore slides leftwards on a pulley control track 17 after the inclination angle of the wellbore is adjusted so as to keep the structure stable; the inclination angle of the wellbore is adjusted to 45° and the test lasts for 15 min.

For comparison, in another experiment, no simulated cuttings are loaded into the cuttings feeding port 9, and no cuttings bed is formed in the simulated wellbore, while the formulation of the drilling fluid, the properties of the rock core, the temperature and pressure in the simulated wellbore, the inclination angle of the wellbore, and the parameters of the stepping drive mechanism and the rotating drive mechanism remain unchanged; the test lasts for 15 min.

The change of the sliding friction force between the drill rod and the cuttings bed, slurry cake, and drilling fluid, etc.

RT443A is lubricant. It can be seen from the data in Table 1: the calculated lubrication coefficient increases obviously after the cuttings bed is taken into consideration, and is more in line with the actual downhole operating condition and provides a more reliable reference for slurry performance adjustment in actual well drilling.

The invention claimed is:
1. An experimental device for testing the lubricity in horizontal well drilling with a cuttings bed taken into consideration, comprising a pulley track, a transparent visual simulated wellbore arranged on the pulley track, with a pulley arranged below one end of the simulated wellbore, a hydraulic cylinder fixedly connected below the other end of the simulated wellbore, and a drill rod mounted at the end connected with the hydraulic cylinder, wherein one end of the drill rod extends into the simulated wellbore, the other end of the drill rod is connected with a stepping drive mechanism and a rotating drive mechanism, and the drill rod is also provided with a thrust sensor and a torque sensor;
a cuttings feeding port is arranged above the simulated wellbore and connected to a slurry tank through a liquid feeding pipeline, and a pressure pump, a second flowmeter and a pressure sensor are sequentially arranged on the liquid feeding pipeline;
a lower end of the simulated wellbore is connected with a liquid return pipeline leading to the slurry tank, and a temperature-reducing and pressure-reducing mecha- nism, a first flowmeter and a transfer pump are sequentially arranged on the liquid return pipeline;

an ultrasonic probe configured to detect a thickness and a flatness of the cuttings bed is arranged on an outer wall of the simulated wellbore, a rock core holder is fixedly connected at the end of the simulated wellbore where the pulley is arranged, a heating mechanism is arranged on the upper part of the rock core holder, a rock core is arranged on a lower part of the rock core holder, and a pressure mechanism is arranged at a lower side of the rock core; a cuttings lifting platform is provided at an inner side of a lower wall of the simulated wellbore and connected to a cuttings bed control center.

2. The experimental device for testing the lubricity in horizontal well drilling with the cuttings bed according to claim 1, wherein power of the hydraulic cylinder comes from a hydraulic pump, which consists of a pump body, a plunger and an operating handle, an oil tank is connected with the hydraulic cylinder and the hydraulic pump through an oil pipe respectively, a first check valve is arranged between the oil tank and the hydraulic pump and a second check valve is arranged between the hydraulic pump and the hydraulic cylinder respectively, and a stop valve is arranged between the oil tank and the hydraulic cylinder.

3. The experimental device for testing the lubricity in horizontal well drilling with the cuttings bed according to claim 1, wherein a rubber ring is arranged at a joint between the simulated wellbore and the drill rod for sealing the joint.

4. The experimental device for testing the lubricity in horizontal well drilling with the cuttings bed according to claim 1, wherein the temperature-reducing and pressure-reducing mechanism is arranged on an initial section of the liquid return pipeline and consists of an electric temperature-reducing and pressure-reducing valve, a safety valve, a pressure meter, a thermometer, a check valve, an electric regulating valve, a throttle valve, a stop valve, a transition pipe, a temperature-reducing water pipe and flange fasteners.

5. The experimental device for testing the lubricity in horizontal well drilling with the cuttings bed according to claim 1, wherein the heating mechanism comprises an electric heating jacket and a temperature controller connected with the electric heating jacket and a temperature sensor respectively, and the heating temperature of the electric heating jacket is adjusted by means of the temperature controller, thereby a temperature in a visual experimental drilling system of the experimental device is controlled and a temperature environment of deep well drilling is simulated.

6. The experimental device for testing the lubricity in horizontal well drilling with the cuttings bed according to claim 1, wherein an inclination angle of the simulated wellbore is adjusted steplessly within a range of 0°-90°.

7. The experimental device for testing the lubricity in horizontal well drilling with the cuttings bed according to claim 1, wherein the pressure mechanism comprises a piston cylinder and a mechanical booster pump configured to supply pressure to the piston cylinder, wherein the mechanical booster pump is connected with a rodless cavity end of the piston cylinder, and a piston rod of the piston cylinder passes through the rock core holder and abuts against the rock core to provide pressure for frictional drilling between the drill rod and a filter cake formed on a surface of the rock core.

8. The experimental device for testing the lubricity in horizontal well drilling with the cuttings bed according to claim 1, wherein a cuttings recovery tank with a filter screen is arranged above the slurry tank, and a stirrer is arranged in the slurry tank.

9. The experimental device for testing the lubricity in horizontal well drilling with the cuttings bed according to claim 1, wherein a differential pressure transmitter configured to detect a pressure difference between the two ends of the simulated wellbore is further arranged on the simulated wellbore, wherein connectors at two ends of the differential pressure transmitter are connected to an inner wall of the simulated wellbore through the simulated wellbore to measure the pressure difference between the two ends of the wellbore; the differential pressure transmitter, the pressure sensor, the ultrasonic probe, the first flowmeter, the second flowmeter, the thrust sensor, the torque sensor, a temperature sensor and a temperature controller are connected to a calculation and display unit through data wires for displaying various detection data and calculating a sliding friction coefficient between the drill rod and the filter cake.

\* \* \* \* \*